United States Patent [19]
Kirka et al.

[11] Patent Number: 5,488,308
[45] Date of Patent: Jan. 30, 1996

[54] APPARATUS AND METHOD FOR DETECTING BREAKAGE OF A DRIVE BAND IN A PACKAGING MACHINE

[76] Inventors: Arde Kirka, 1100 Tanglewood, Algonquin, Ill. 60102; David Persells, 613 Torrey Pines, Twin Lakes, Wis. 53181; Roland Andersson, 2786 Old Buffalo Grove Rd., Arlington Heights, Ill. 60004; Shigehiro Kinoshita, 1124 Johnson Dr., Apt. 3536, Buffalo Grove, Ill. 60089

[21] Appl. No.: 277,614

[22] Filed: Jul. 20, 1994

[51] Int. Cl.$^6$ .................................................... G01R 31/00
[52] U.S. Cl. ........................... 324/555; 324/500; 324/511
[58] Field of Search ..................................... 324/500, 511, 324/537, 555, 756; 361/1; 340/532

[56] References Cited

U.S. PATENT DOCUMENTS

| | | | |
|---|---|---|---|
| 4,813,320 | 3/1989 | Malloy et al. | 83/61 |
| 4,862,095 | 8/1989 | Yamamoto et al. | 324/543 |
| 5,083,087 | 1/1992 | Fox et al. | 324/537 |

*Primary Examiner*—Kenneth A. Wieder
*Assistant Examiner*—Glenn W. Brown
*Attorney, Agent, or Firm*—McAndrews, Held & Malloy Ltd.

[57] ABSTRACT

An apparatus and method for detecting the breakage of an electrically conductive drive band are disclosed. The apparatus includes an electrically conductive probe that is disposed proximate of the electrically conductive band. The probe is spaced from the electrically conductive drive band to allow the probe to contact the band upon its breakage. The band is connected to electrical ground potential. The apparatus also includes a continuity checking circuit that is connected to the electrically conductive drive band and the probe. The continuity checking circuit is designed so that the electrically conductive probe does not have a voltage potential thereon during normal operation of the apparatus. When the band breaks, it contacts the probe and thereby establishes an electrical continuity between the band and the probe. This electrical continuity is detected by the continuity checking circuit to provide a signal output indicative of the breakage of the band.

45 Claims, 5 Drawing Sheets

APPARATUS AND METHOD FOR DETECTING BREAKAGE OF A DRIVE BAND IN A PACKAGING MACHINE

TECHNICAL FIELD

The present invention relates to the detection of the breakage of a band. More specifically, the present invention relates to an apparatus and method for detecting the breakage of an electrically conductive drive band used to drive a mechanism, such as a lifter mechanism, in a packaging machine.

BACKGROUND

Numerous machines utilize drive bands for driving various mechanisms disposed within the machine. Significant damage to the machine may occur upon the breakage of the drive band, particularly when the breakage goes undetected. In such instances, further operation of the machine increases the damage and/or increases the likelihood of further, potentially irreparable, machine damage.

To mitigate damage to the machine, the machine should be shut down immediately when a band breaks. Therefore, it is useful to detect the band breakage and to provide a signal which can be used to shut the machine down upon its detection.

Such detection may, for example, be accomplished by placing an infrared emitter and detector on opposite sides of the band. In normal operation, the infrared beam that is emitted by the infrared emitter is blocked by the presence of the drive band. Upon band breakage, the drive band may move to a position in which the infrared beam is no longer blocked. The infrared beam may then be detected by the infrared detector. The detector output may be subject to further processing to provide a signal output that is indicative of band breakage. The resulting signal may be used, for example, to shut down the machine and prevent further damage.

Such an infrared detection scheme may be relatively costly to implement and, further, may be subject to various problems depending on the particular machine type and the particular implementation of the drive band. For example, such an infrared detection device may not be appropriate for use in an environment in which either the emitter or detector is subject to contaminants that may cover their respective lenses and thereby inhibit the ability of the device to detect a drive band breakage. This is true of packaging machines where the emitter and/or detector may be subject to the contaminant material that sloshes or aerates from the containers.

Additionally, such a detection device may be inappropriate for use in situations in which the motion and physical design of the drive band is such that a discontinuity of the band does not occur in the region of the detector when the band breaks. In such situations, the band may break but may nevertheless continue to block detection of the infrared beam by the detector. The infrared device would thus continue to signal a normal operating condition despite the band break.

In packaging machines, there is a requirement that the interior of the machine remain generally hygienic. An infrared detection device, such the one as described above, may have wires or other components that are exposed to the interior of the machine and which may compromise the hygiene of the machine. Further, such exposed components compromise the safety of the machine as well, particularly if the exposed components have power supplied to them.

SUMMARY OF THE INVENTION

An apparatus and method for detecting the breakage of an electrically conductive drive band are disclosed. The apparatus includes an electrically conductive probe that is disposed proximate of the electrically conductive band. The probe is spaced from the electrically conductive drive band to allow the probe to contact the band when the band breaks. The band may be connected to electrical ground potential, for example, earth or chassis ground.

The apparatus also includes a continuity checking circuit that is connected to the electrically conductive drive band and the probe. The continuity checking circuit is designed so that it does not provide a voltage potential to either the drive band or the probe.

When the band breaks, it contacts the probe and thereby establishes an electrical continuity between the band and the probe. This electrical continuity is detected by the continuity checking circuit to provide a signal output indicative of the breakage of the band.

In accordance with one embodiment of the apparatus, the continuity checking circuit comprises a continuity relay connected between the probe and the band for actuation by electrical contact between the band and the probe.

In accordance with a further embodiment of the apparatus, a further electrically conductive probe is disposed on the side of the band opposite the first mentioned probe. The further probe is electrically connected to the first mentioned probe and is spaced from the band to facilitate contact between the further probe and the drive band upon breakage of the drive band.

Since the contact between the probe(s) and the drive band may have a relatively short duration, the signal output from the continuity checking circuit may likewise have a relatively short duration. As such, it is possible that the band breakage may go undetected.

To enhance detection of the band breakage signal, the signal output of the continuity checking circuit may be received by a latching circuit that provides an extended signal output indicative of the breakage of the electrically conductive band. The latching circuit may comprise a latching relay that includes a SET input connected to receive the signal output of the continuity checking circuit and a RESET input for receiving a signal, for example, from a programmable logic controller ("PLC"), to reset the latching relay from its set condition. Alternatively, a pulse extender circuit designed from standard integrated circuits may be used to extend the output signal.

To facilitate reliability of operation, the apparatus may include a test circuit for testing the operation of the continuity checking circuit. The test circuit may comprise a relay that is connected between the electrically conductive probe and the electrically conductive band. Actuation of the relay by, for example, a PLC, may cause electrical continuity between the probe and the band. The actuation may be detected either directly or indirectly by, for example, the PLC.

In an exemplary embodiment, the apparatus may be used to detect the breakage of a drive band for a lifter mechanism of a packaging machine. The disclosed apparatus reliably detects band breakage without compromising the safety or hygiene of the interior of the packaging machine. Additionally, the apparatus may be implemented at a minimal cost in comparison to other detection devices.

Other objects and advantages of the present invention will become apparent upon reference to the accompanying detailed description when taken in conjunction with the following drawings.

DETAILED DESCRIPTION OF THE PREFERRED EMBODIMENT

Figure 1:
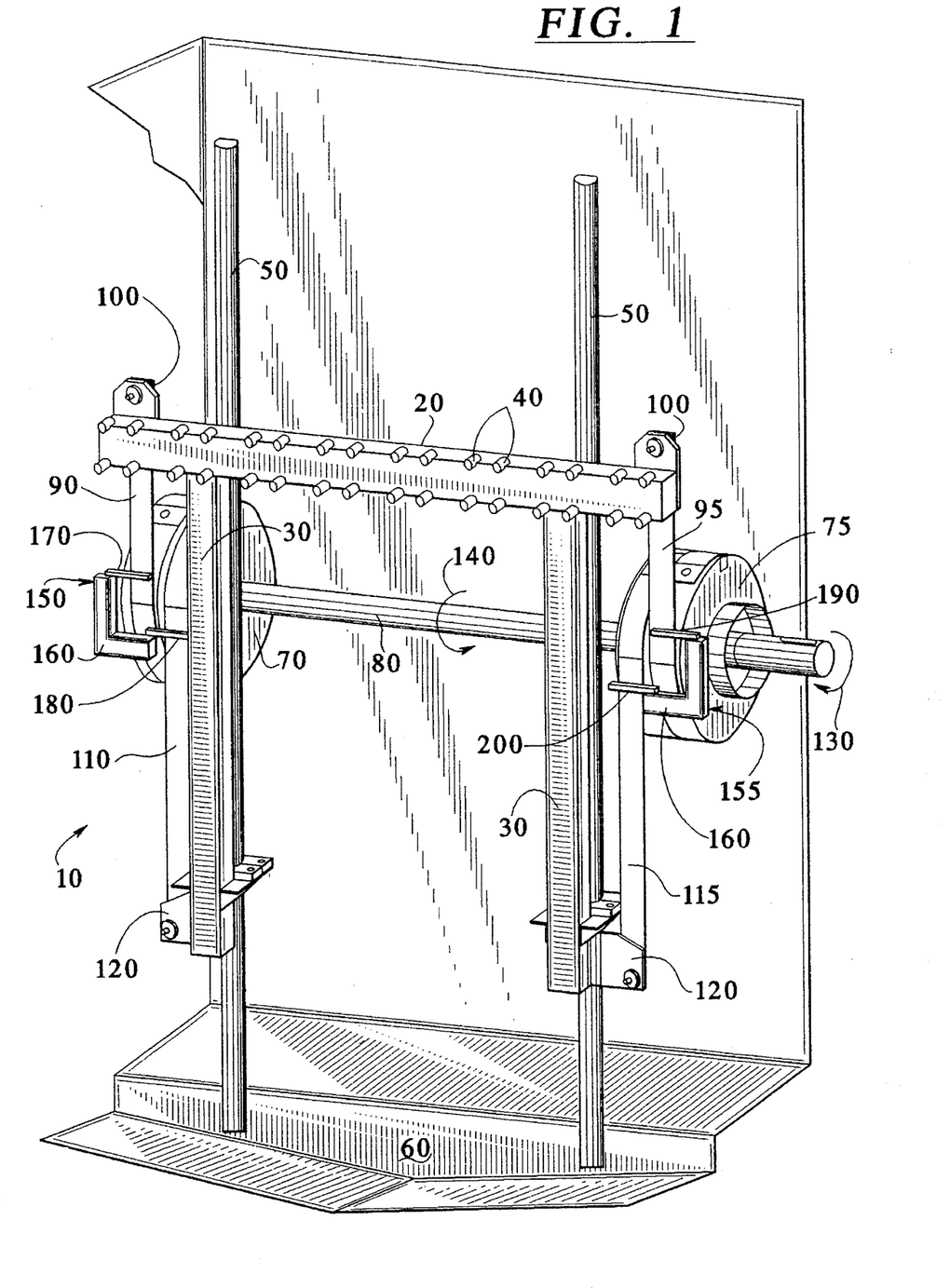
FIGS. 1–3 are perspective views of a lifter mechanism having drive belts which may be sensed by the disclosed detection apparatus.
Figure 2:
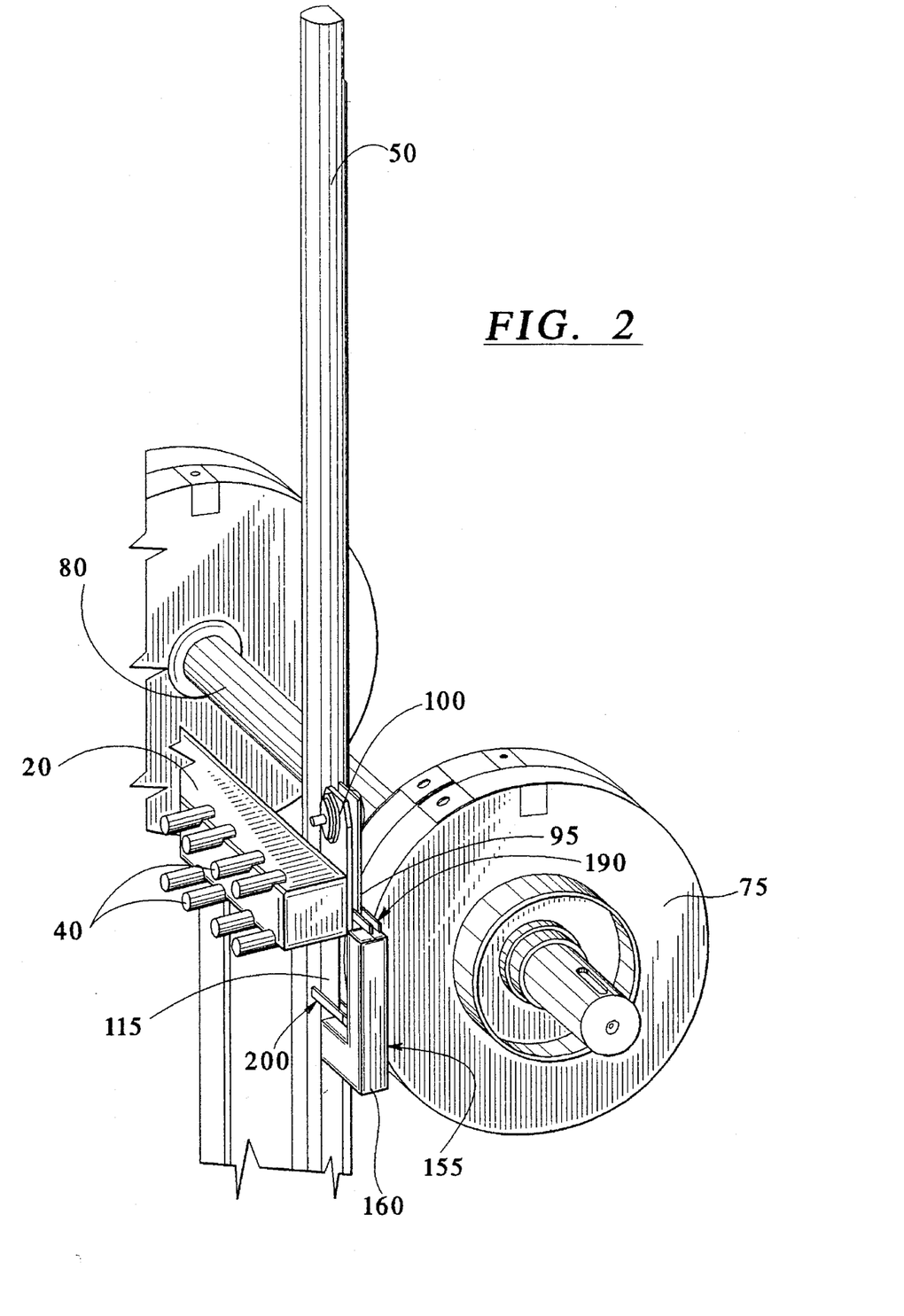
Figure 3:
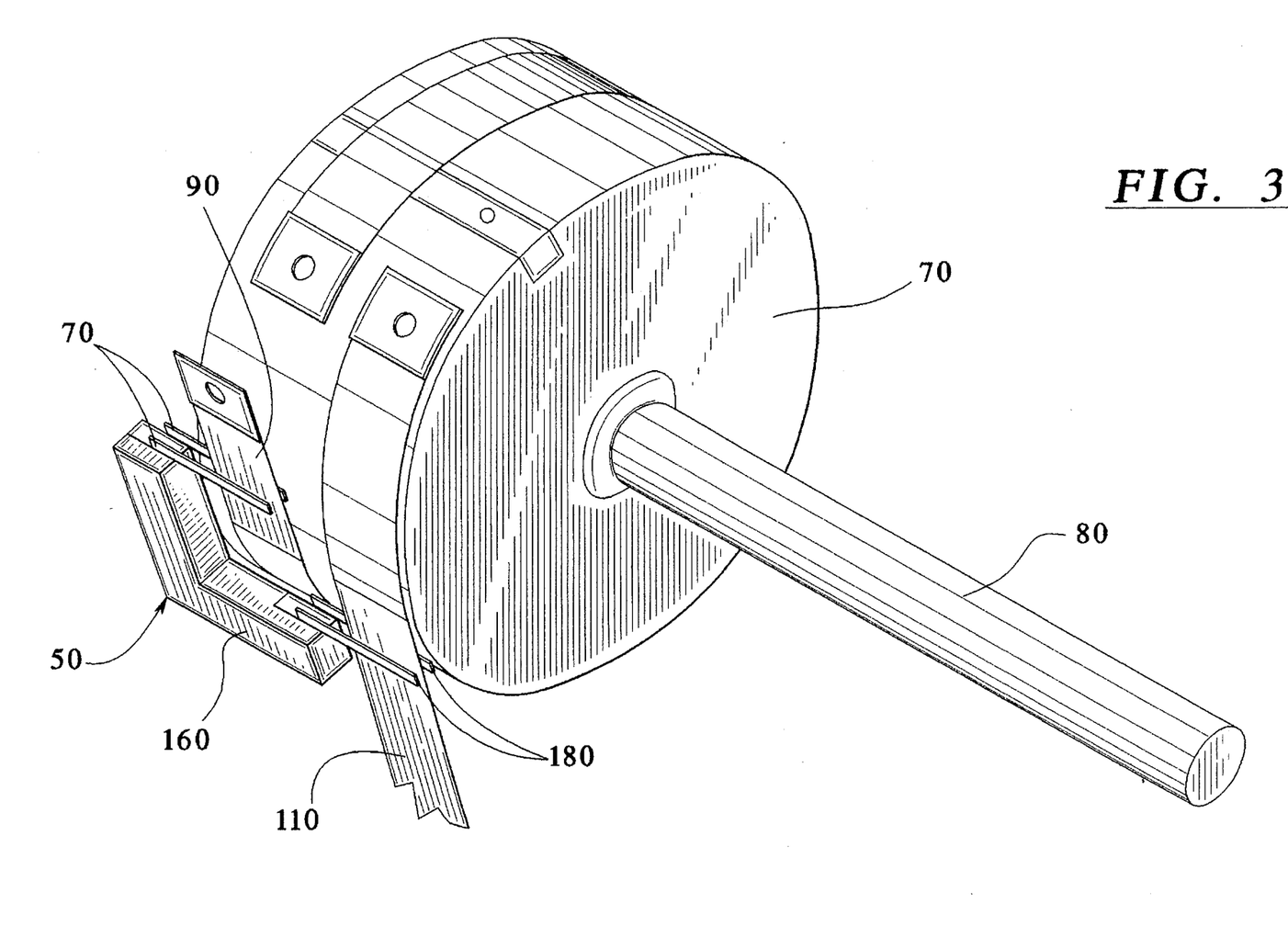

A lifter mechanism, shown generally at 10, is illustrated in FIGS. 1–3. The lifter mechanism 10 includes a horizontally disposed lifter bar 20 and a pair of spaced apart vertical legs 30 extending from the lifter bar 20. The lifter bar 20 includes a plurality of pegs 40 that extend horizontally to engage, for example, the bottoms of cartons in a packaging machine. A pair of vertically disposed guide rods 50 extend from a base 60 and engage the vertical legs 30 in a manner that allows the vertical legs 30 to slide along the guide rods 50.

A pair of drive rollers 70, 75 are disposed on opposite ends of a shaft 80 in a region exterior of the guide rods 50. Each of the drive rollers 70, 75 has respective electrically conducting drive bands 90, 95 that extend about the drive rollers 70, 75 in a clockwise direction to engage tabs 100 on the lifter bar 20. Each of the drive rollers 70, 75 also have respective further drive bands 110, 115 that extend about the circumference of the respective drive rollers 70, 75 in a counterclockwise direction to engage tabs 120 on the vertical legs 30.

In operation, the shaft 80 is driven, for example, by a servomotor, in a cyclic fashion in both the clockwise and counterclockwise directions. When the shaft 80 is rotated in the clockwise direction, illustrated by arrow 130, the drive bands 110, 115 become shorter and exert an upward force on vertical legs 30 to cause the legs 30 and the lifter bar to proceed in an upward direction. At the same time, the drive bands 90, 95 are unrolled from the drive rollers 70, 75 and are effectively lengthened. When the shaft 80 is rotated in the counterclockwise direction, illustrated at arrow 140, the drive bands 110, 115 are unrolled from the respective drive rollers while the drive bands 90, 95 are rolled onto the respective drive rollers 70, 75. This effectively increases the length of drive bands 110, 115 and decreases the length of drive bands 90, 95 such that drive bands 90, 95 exert a downward force on the lifter bar 20 and cause the lifter bar 20 and the vertical legs 30 to slide in a downward direction along guide rods 50. The cyclic clockwise and counterclockwise rotation of the shaft 80 occurs at a high rate of speed.

Breakage of any of the bands 90, 95, 110, 115 may disrupt the operation of the lifter mechanism 10 or may result in its complete failure. Such a failure may disrupt the operation of the entire packaging machine and/or may cause significant damage. As such, an apparatus for detecting the breakage of a band is employed.

The band failure detection apparatus, as implemented on the lifter mechanism 10, includes two probe modules 150, 155. Each probe module includes a generally L-shaped mounting bracket 160. Probe pairs 170, 180, 190, 200 are respectively associated with each of the drive bands 90, 95, 110, 115. Each probe of the probe pairs 170, 180, 190, 200, as illustrated in FIGS. 2 and 3, is in the form of an elongated, electrically conductive pin that extends from the L-shaped mounting bracket in a horizontal direction. The probes of each probe pair are disposed on opposite sides of and in close proximity with the respective drive band to facilitate contact between one or more of the probes and the respective band upon breakage of the respective band.

Figures 4, 5:
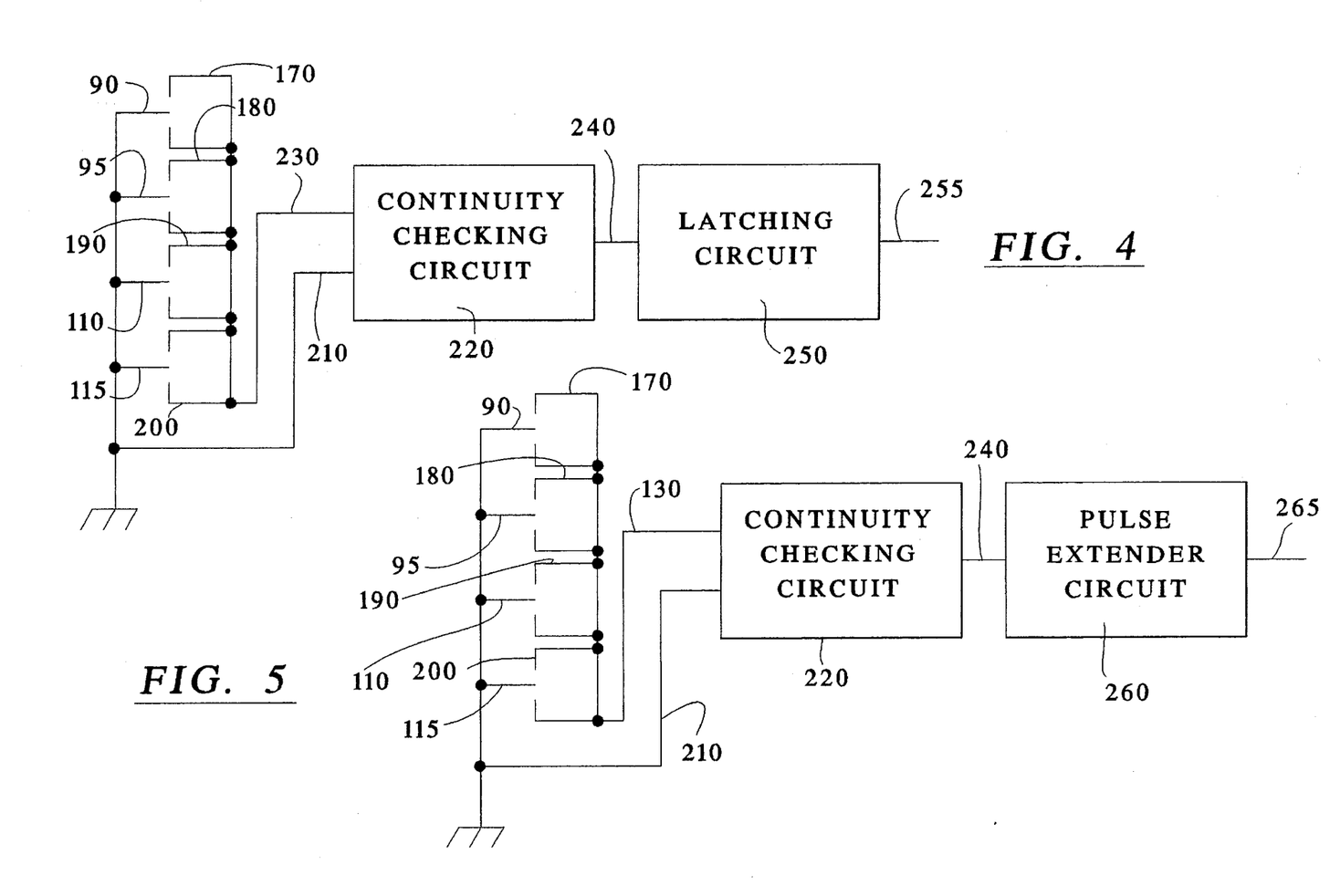
FIG. 4 is a schematic block diagram of one embodiment of the disclosed detection apparatus.
FIG. 5 is a schematic block diagram of a further embodiment of the disclosed detection apparatus.

FIG. 4 is a schematic block diagram illustrating the electronic circuitry that may be used in the disclosed band breakage detection apparatus. The apparatus includes bands 90, 95, 110, and 115 and probe pairs 170, 180, 190, and 200. The bands 90, 95, 110, and 115 are electrically connected to one another to ground potential. Line 210 connects the bands 90, 95, 110, and 115 to the input of a continuity checking circuit 220 while probe pairs 170, 180, 190, and 200 are connected to the continuity checking circuit 220 by line 230. The continuity checking circuit 220 is designed so that there is no voltage potential placed on either lines 210 or 230 during normal operation.

When any of the bands 90, 95, 110, 115 break, the broken band contacts one or more of the probes of probe pairs 170, 180, 190, or 200 thereby resulting in an electrical continuity between the probe pairs 170, 180, 190, 200 and the bands 90, 95 110, 115. This electrical continuity is detected by the continuity checking circuit 220 which, in turn, provides a signal output on output line 240 indicative of band breakage.

Upon band breakage, the contact between the broken band and the probe may be of a relatively short duration. As a result, the signal output on line 240 that is indicative of the band breakage will likewise have a relatively short duration and thus may escape detection. Therefore, it may be desirable to supply the signal output on line 240 to the input of a latching circuit 250. The latching circuit 250 provides a bistable, extended signal output on line 255 so that the occurrence of a band breakage may be reliably detected.

FIG. 5 illustrates an alterative embodiment of the apparatus wherein the signal output on line 240 is supplied to the input of a pulse extender circuit 260 which, for example, may be implemented with a 555 timer IC. The pulse extender circuit 260 effectively extends the duration of the signal output on line 240 so that band breakage may be reliably detected for a specified period of time after the band has broken. Unlike the latching circuit 250, however, the output signal on line 265 of the pulse extender circuit 260 is monostable. The signal output on line 265 from the pulse extender circuit 260 is thus generated as a pulse of a predetermined duration.

Figure 6:
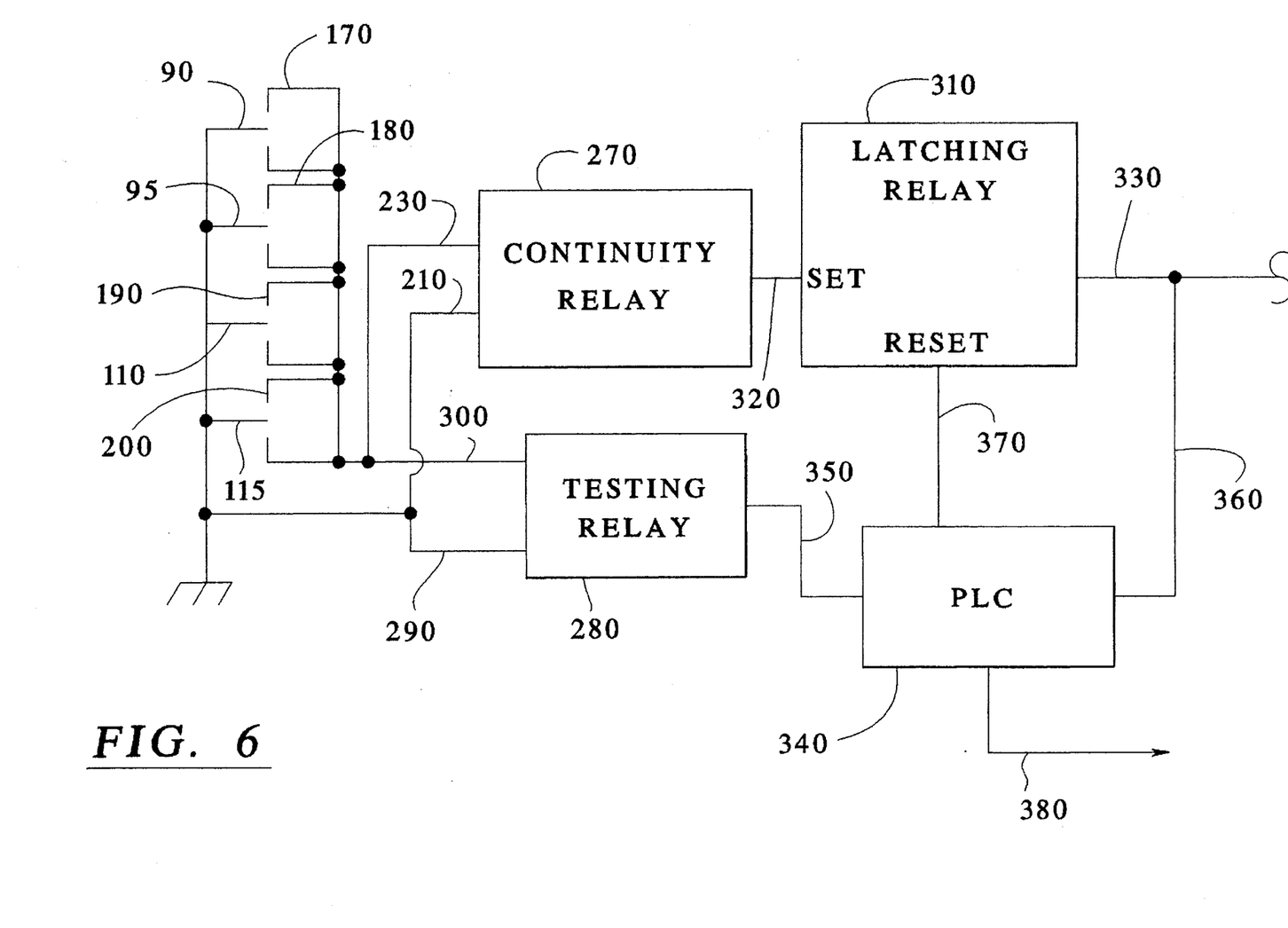
FIG. 6 is a more detailed schematic block diagram of the embodiment illustrated in FIG. 4.

FIG. 6 is a more detailed block diagram of the circuit of FIG. 4 and further includes testing circuitry. As illustrated, the bands 90, 95, 110, 115 and probe pairs 170, 180, 190, 200 are connected to a continuity relay 270 by lines 210 and 230 respectively. The bands 90, 95, 110, 115 and probe pairs 170, 180, 190, 200 are also connected to a testing relay 280 by lines 210 and 230 respectively. The switched output of the continuity relay 270 is supplied to the SET input of a latching relay 310 by line 320. The switched output of the latching relay 310 on line 330, in turn, indicates the occurrence of a band breakage and may be used, for example, to shut down the machine.

To assure reliability of operation, the circuit of FIG. 6 utilizes test circuitry that includes testing relay 280 and PLC 340. Upon system initialization and/or periodically during the operation of the apparatus, the testing relay 280 is actuated by a signal output on line 350 of the PLC 340. Actuation of the testing relay results in an electrical continuity between bands 90, 95, 110, 115 and probe pairs 170, 180, 190, 200. This electrical continuity actuates the continuity relay 270 which, in turn, actuates the latching relay 310 at its SET input. Upon detection of the actuation of the latching relay 310 by the PLC 340 along line 360, the PLC 340 returns the testing relay 280 to a non-actuated state and resets latching relay 310 by sending a signal to the RESET input at line 370. If the PLC 340 fails to detect actuation of the latching relay 310, the PLC 340 may provide a fail signal output at line 380.

In the exemplary embodiment of the apparatus illustrated in FIG. 6, the continuity relay 270 may be a continuity relay manufactured by and available from the Schiele Corporation. The latching relay 310 may be a HC2K-DC-24V relay manufactured by and available from Aeromat Corporation. The testing relay 280 may be any standard off-the-shelf relay. The PLC 340 may be a PLC manufactured by and available from General Electric, Fanucor, or any other PLC manufacturer.

Although the present invention has been described with reference to a specific embodiment, those of skill in the art will recognize that changes may be made thereto without departing from the scope and spirit of the invention as set forth in the appended claims.

We claim as our invention:

1. An apparatus for detecting breakage of an electrically conductive band, the apparatus comprising:
   a) an electrically conductive probe disposed proximate the electrically conductive band and spaced from the electrically conductive band to facilitate electrical contact between the probe and the electrically conductive band upon breakage of the electrically conductive band, the electrically conductive band being connected to ground;
   b) a continuity checking circuit connected to the electrically conductive band and the electrically conductive probe, the electrically conductive probe connected to the continuity checking circuit so that the electrically conductive probe does not have a voltage potential thereon during normal operation of the apparatus, contact between the electrically conductive probe and the electrically conductive band resulting in electrical continuity therebetween, the electrical continuity being detected by the continuity checking circuit to provide a signal output indicative of the breakage of the electrically conductive band.

2. An apparatus as claimed in claim 1 wherein the continuity checking circuit comprises a continuity relay connected between the electrically conductive probe and the electrically conductive band for actuation by electrical contact between the electrically conductive band and the electrically conductive probe.

3. An apparatus as claimed in claim 1 and further comprising a further electrically conductive probe, the electrically conductive probe and the further electrically conductive probe disposed on opposite sides of the electrically conductive band, the further probe spaced from the electrically conductive band to facilitate electrical contact between the further electrically conductive probe and the electrically conductive band, the electrically conductive probe and the further electrically conductive probe being electrically connected to one another to an input of the continuity checking circuit.

4. An apparatus as claimed in claim 1 wherein the signal output of the continuity checking circuit is connected to a latching circuit that provides an extended signal output indicative of the breakage of the electrically conductive band.

5. An apparatus as claimed in claim 4 wherein the latching circuit comprises a latching relay.

6. An apparatus as claimed in claim 5 wherein the latching relay includes a set input connected to receive the signal output from the continuity checking circuit and a reset input for receiving a signal to reset the latching relay from its set condition.

7. An apparatus as claimed in claim 1 wherein the signal output of the continuity checking circuit is connected to a pulse extender circuit.

8. An apparatus as claimed in claim 1 and further comprising a test circuit connected to provide a short circuit between the electrically conductive band and the electrically conductive probe for testing of the continuity checking circuit.

9. An apparatus as claimed in claim 8 wherein the test circuit comprises a relay connected between the electrically conductive probe and the electrically conductive band, actuation of the relay causing electrical continuity between the electrically conductive probe and the electrically conductive band.

10. In a packaging machine including a mechanical device driven by an electrically conductive drive band, an apparatus for detecting breakage of the drive band, the apparatus comprising:
    a) an electrically conductive probe disposed proximate the drive band and spaced from the drive band to facilitate contact between the probe and the drive band upon breakage of the drive band, the drive band being connected to ground;
    b) a continuity checking circuit connected to the drive band and the electrically conductive probe, the continuity checking circuit connected to the electrically conductive probe so that the electrically conductive probe does not have a voltage potential thereon during normal operation of the apparatus, electrical contact between the electrically conductive probe and the drive band being detected by the continuity checking circuit to provide a signal output indicative of the breakage of the drive band.

11. An apparatus as claimed in claim 10 wherein the continuity checking circuit comprises a continuity relay connected between the electrically conductive probe and the drive band for actuation by electrical contact between the drive band and the electrically conductive probe.

12. An apparatus as claimed in claim 10 and further comprising a further electrically conductive probe, the electrically conductive probe and the further electrically conducting probe being disposed on opposite sides of the drive band, the further probe spaced from the drive band to allow electrical contact between the further electrically conductive probe and the drive band upon breakage of the drive band, the electrically conductive probe and the further electrically conductive probe being electrically connected to each another.

13. An apparatus as claimed in claim 10 wherein the signal output of the continuity checking circuit is connected to a latching circuit that provides an extended signal output indicative of the breakage of the drive band.

14. An apparatus as claimed in claim 13 wherein the latching circuit comprises a latching relay.

15. An apparatus as claimed in claim 14 wherein the latching relay includes a set input connected to receive the signal output from the continuity checking circuit and a reset input for receiving a signal to reset the latching relay from its set condition.

16. An apparatus as claimed in claim 10 wherein the signal output of the continuity checking circuit is connected for receipt by a pulse extender circuit.

17. An apparatus as claimed in claim 10 and further comprising a test circuit connected to provide a short circuit between the electrically conductive band and the electrically conductive probe for testing of the continuity checking circuit.

18. An apparatus as claimed in claim 17 wherein the test circuit comprises a relay connected between the electrically conductive probe and the drive band, actuation of the relay causing electrical continuity between the electrically conductive probe and the drive band.

19. In a packaging machine including a mechanical device driven by an electrically conductive drive band, an apparatus for detecting breakage of the drive band, the apparatus comprising:
   a) a first electrically conductive probe disposed on a first side of the drive band and spaced from the drive band to facilitate contact between the first probe and the drive band upon breakage of the drive band, the drive band being connected to ground;
   b) a second electrically conductive probe disposed on a second side of the drive band and spaced from the drive band to facilitate contact between the second probe and the drive band upon breakage of the drive band, the first and second probes being electrically connected to one another;
   c) a continuity checking circuit connected to the drive band and the first and second probes, the first and second probes being connected to the continuity checking circuit so that the first and second probes do not have a voltage potential thereon during normal operation of the apparatus, electrical contact between at least one of the first and second probes and the drive band being detected by the continuity checking circuit to provide a signal output indicative of the breakage of the drive band;
   d) signal extension means connected to the signal output of the continuity checking circuit for providing an extended signal output indicative of the breakage of the drive band.

20. An apparatus as claimed in claim 19 wherein the continuity checking circuit comprises a continuity relay connected between the first and second probes and the drive band for actuation by electrical contact between the drive band and at least one of the first and second probes.

21. An apparatus as claimed in claim 19 wherein the signal extension means comprises a latching relay connected to receive the signal output from the continuity checking circuit.

22. An apparatus as claimed in claim 21 wherein the latching relay includes a set input connected to receive the signal output from the continuity checking circuit and a reset input for receiving a signal to reset the latching relay from its set condition.

23. An apparatus as claimed in claim 19 wherein the signal extension means is a pulse extender circuit.

24. An apparatus as claimed in claim 19 and further comprising a test circuit connected to provide a short circuit between the electrically conductive band and the electrically conductive probe for testing of the continuity checking circuit.

25. An apparatus as claimed in claim 24 wherein the test circuit comprises a relay connected between the first and second probes and the drive band, actuation of the relay causing electrical continuity between the first and second probes and the drive band.

26. In a lifter mechanism for lifting containers in a packaging machine, the lifter mechanism including a guide shaft, a lifter bar disposed on said guide shaft, the lifter bar being driven at least by first and second electrically conductive drive bands that are connected to opposite sides of a drive wheel, an apparatus for detecting breakage of either the first or second drive band, the apparatus comprising:
   a) a first electrically conductive probe disposed on a first side of the first drive band and spaced from the first drive band to facilitate contact between the first probe and the first drive band upon breakage of the first drive band, the first drive band being connected to ground;
   b) a second electrically conductive probe disposed on a second side of the first drive band and spaced from the first drive band to facilitate contact between the second probe and the first drive band upon breakage of the first drive band;
   c) a third electrically conductive probe disposed on a first side of the second drive band and spaced from the second drive band to facilitate contact between the third probe and the second drive band upon breakage of the second drive band, the second drive band being connected to ground;
   d) a fourth electrically conductive probe disposed on a second side of the second drive band and spaced from the second drive band to facilitate contact between the fourth probe and the second drive band upon breakage of the second drive band, the first, second, third, and fourth probes being electrically connected to one another;
   e) a continuity checking circuit connected to the first and second drive bands and the probes, the continuity checking circuit connected to the probes so that the probes do not have a voltage potential thereon during normal operation of the apparatus, electrical contact between at least one of the probes and the broken drive band being detected by the continuity checking circuit to provide a signal output indicative of the breakage of the broken drive band;
   f) signal extension means connected to the signal output from the continuity checking circuit for providing an extended signal output indicative of the breakage of the broken drive band.

27. An apparatus as claimed in claim 26 wherein the probes are mounted to a generally L-shaped mounting bracket, the first and second probes being connected to a first end of the generally L-shaped mounting bracket, the third and fourth probes being connected to a second end of the generally L-shaped mounting bracket.

28. An apparatus as claimed in claim 26 wherein the continuity checking circuit comprises a continuity relay connected between the probes and the drive bands for actuation by electrical contact between a broken drive band and at least one of the probes.

29. An apparatus as claimed in claim 26 wherein the signal extension means comprises a latching relay connected to receive the signal output from the continuity checking circuit.

30. An apparatus as claimed in claim 29 wherein the latching relay includes a set input connected to receive the signal output from the continuity checking circuit and a reset input for receiving a signal to reset the latching relay from its set condition.

31. An apparatus as claimed in claim 26 wherein the signal extension means comprises a pulse extender circuit connected to receive the signal output from the continuity checking circuit.

32. An apparatus as claimed in claim 26 and further comprising a test circuit connected to provide a short circuit between the electrically conductive bands and the electrically conductive probes for testing of the continuity checking circuit.

33. An apparatus as claimed in claim 32 wherein the test circuit comprises a relay connected between the probes and the drive bands, actuation of the relay causing electrical continuity between the probes and the drive bands.

34. A method for detecting breakage of an electrically conductive drive band, the method comprising the steps of:
   a) placing an electrically conductive probe proximate the electrically conductive band and spaced from the electrically conductive band to allow the probe to contact the electrically conductive band when the band breaks;
   b) monitoring for electrical continuity between the electrically conductive probe and the electrically conducting band;
   c) providing an output signal to indicate band breakage upon detection of electrical continuity between the electrically conductive probe and the electrically conductive band.

35. A method as claimed in claim 34 wherein the step of monitoring is further defined by monitoring for electrical continuity between the electrically conductive probe and the electrically conducting band without placing a voltage potential on either the electrically conducting probe or the electrically conductive band.

36. A method as claimed in claim 34 and further comprising the step of extending the duration of the output signal.

37. An apparatus for detecting breakage of an electrically conductive band, the apparatus comprising:
   a) an electrically conductive probe disposed proximate the electrically conductive band and spaced from the electrically conductive band to facilitate electrical contact between the probe and the electrically conductive band upon breakage of the electrically conductive band, the electrically conductive band being connected to ground;
   b) a continuity checking circuit connected to the electrically conductive band and the electrically conductive probe, contact between the electrically conductive probe and the electrically conductive band resulting in electrical continuity therebetween, the electrical continuity being detected by the continuity checking circuit to provide a signal output indicative of the breakage of the electrically conductive band.

38. An apparatus as claimed in claim 37 wherein the continuity checking circuit comprises a continuity relay connected between the electrically conductive probe and the electrically conductive band for actuation by electrical contact between the electrically conductive band and the electrically conductive probe.

39. An apparatus as claimed in claim 37 and further comprising a further electrically conductive probe, the electrically conductive probe and the further electrically conductive probe disposed on opposite sides of the electrically conductive band, the further probe spaced from the electrically conductive band to facilitate electrical contact between the further electrically conductive probe and the electrically conductive band, the electrically conductive probe and the further electrically conductive probe being electrically connected to one another to an input of the continuity checking circuit.

40. An apparatus as claimed in claim 37 wherein the signal output of the continuity checking circuit is connected to a latching circuit that provides an extended signal output indicative of the breakage of the electrically conductive band.

41. An apparatus as claimed in claim 40 wherein the latching circuit comprises a latching relay.

42. An apparatus as claimed in claim 41 wherein the latching relay includes a set input connected to receive the signal output from the continuity checking circuit and a reset input for receiving a signal to reset the latching relay from its set condition.

43. An apparatus as claimed in claim 37 wherein the signal output of the continuity checking circuit is connected to a pulse extender circuit.

44. An apparatus as claimed in claim 37 and further comprising a test circuit connected to provide a short circuit between the electrically conductive band and the electrically conductive probe for testing of the continuity checking circuit.

45. An apparatus as claimed in claim 44 wherein the test circuit comprises a relay connected between the electrically conductive probe and the electrically conductive band, actuation of the relay causing electrical continuity between the electrically conductive probe and the electrically conductive band.

* * * * *